US012146886B2

(12) United States Patent
Metz et al.

(10) Patent No.: US 12,146,886 B2
(45) Date of Patent: Nov. 19, 2024

(54) METHODS FOR DETECTING AND TREATING ENDOMETRIOSIS (71) Applicant: The Feinstein Institutes for Medical Research, Manhasset, NY (US)

(72) Inventors: Christine Metz, Great Neck, NY (US); Peter K. Gregersen, Larchmont, NY (US); Laura Warren, Forest Hills, NY (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 1031 days.

(21) Appl. No.: 16/978,141

(22) PCT Filed: Mar. 6, 2019

(86) PCT No.: PCT/US2019/020868
§ 371 (c)(1),
(2) Date: Sep. 3, 2020

(87) PCT Pub. No.: WO2019/173418
PCT Pub. Date: Sep. 12, 2019

(65) Prior Publication Data
US 2021/0096137 A1     Apr. 1, 2021

Related U.S. Application Data (60) Provisional application No. 62/639,112, filed on Mar. 6, 2018.

(51) Int. Cl.
| *C12Q 1/6883* | (2018.01) |
| *A61K 31/57* | (2006.01) |
| *C12Q 1/6844* | (2018.01) |
| *G01N 33/68* | (2006.01) |
| *A61B 17/00* | (2006.01) |
| *A61B 17/42* | (2006.01) |

(52) U.S. Cl.
CPC .......... *G01N 33/689* (2013.01); *A61K 31/57* (2013.01); *C12Q 1/6844* (2013.01); *C12Q 1/6883* (2013.01); *A61B 17/00234* (2013.01); *A61B 2017/4216* (2013.01); *C12Q 2600/158* (2013.01); *G01N 2800/364* (2013.01)

(58) Field of Classification Search
CPC ......... G01N 2800/364; G01N 33/5044; C12Q 2600/158
See application file for complete search history.

(56) References Cited

U.S. PATENT DOCUMENTS

| 2003/0113746 A1 | 6/2003 | Leyendecker |
| 2007/0287676 A1 | 12/2007 | Guo et al. |
| 2008/0318237 A1 | 12/2008 | Giudice |
| 2014/0024557 A1 | 1/2014 | Giudice |
| 2017/0097358 A1 | 4/2017 | Simón et al. |
| 2019/0233893 A1* | 8/2019 | Giudice ............. G01N 33/6893 |

FOREIGN PATENT DOCUMENTS

| EP | 1321768 A1 * | 6/2003 | .......... G01N 33/689 |
| WO | 2011017770 A1 | 2/2011 | |

OTHER PUBLICATIONS

Klemmt et al., "Stromal cells from endometriotic lesions and endometrium from women with endometriosis have reduced decidualization capacity," Fertility and Sterility, March, vol. 85, No. 3, pp. 564-572 (Year: 2006).*
Rossignoli et al., "Isolation, Characterization, and Transduction of Endometrial Decidual Tissue Multipotent Mesenchymal Stromal/Stem Cells from Menstrual Blood," BioMed Research International, pp. 1-14. (Year: 2013).*
Piltonen et al., "Endometrial stromal fibroblasts from women with polycystic ovary syndrome have impaired progesterone-mediated decidualization, aberrant cytokine profiles and promote enhanced immune cell migration in vitro," Human Reproduction, vol. 30 No. 5, pp. 1203-1215. (Year: 2015).*
International Search Report and Written Opinion dated Jun. 3, 2019 from PCT International Appln. No. PCT/US2019/020868.
Klemmt et al., "Stromal Cells From Endometriotic Lesions and Endometrium From Women With Endometriosis Have Reduced Decidualization Capacity," Fertil. Steril., vol. 85, No. 3, Mar. 2006, pp. 564-572.
Aghajanova et al., "The Protein Kinase a Pathway-Regulated Transcriptome of Endometrial Stromal Fibroblasts Reveals Compromised Differentiation and Persistent Proliferative Potential in Endometriosis," Endocrinology, vol. 151, No. 3, Mar. 2010, pp. 1341-1355.
Warren et al., "Analysis of Menstrual Effluent: Diagnostic Potential for Endometriosis," Molecular Medicine, vol. 24, No. 1, 2018.
Ahn et al., "cAMP-Response Element-Binding 3-Like Protein 1 (CREB3L1) is Required for Decidualization and Its Expression is Decreased in Women With Endometriosis," Curr. Mol. Med., vol. 16, No. 3, 2016, pp. 276-287.
Darzi et al., "Osteogenic Differentiation of Stem Cells Derived from Menstrual Blood Versus Bone Marrow in the Presence of Human Platelet Releasate," Tissue Engineering, Part A, vol. 18, Nos. 15 and 16, Jun. 25, 2012, pp. 1720-1728.
Nikoo et al., "Menstrual Blood-Derived Stromal Stem Cells From Women With and Without Endometriosis Reveal Different Phenotypic and Functional Characteristics," Molecular Human Reproduction, vol. 20, No. 9, Jun. 16, 2014, pp. 905-918.

(Continued)

*Primary Examiner* — Young J Kim
(74) *Attorney, Agent, or Firm* — Amster, Rothstein & Ebenstein LLP (57) ABSTRACT

Provided is a method of non-invasively diagnosing endometriosis in a subject comprising maintaining or culturing stromal cells, obtained from a menstrual effluent or discharge sample from the subject. Also provided is a method of non-invasively diagnosing fertility in a subject. Also provided is a kit for non-invasively diagnosing endometriosis in a subject. Also provided is a method of treating endometriosis in a subject. Also provided is a method of preventing the progression or development of endometriosis in a subject.

11 Claims, 4 Drawing Sheets

Specification includes a Sequence Listing.

(56) References Cited

OTHER PUBLICATIONS

Extended EP Search Report dated Dec. 14, 2021 from European Patent Application EP 19763950.
Lee et al., "Phosphatidic Acid Induces Decidualization by Stimulating Akt-PP2A Binding in Human Endometrial Stromal Cells," The FEBS Journal, vol. 283, No. 22, 2016, pp. 4163-4175.
Rossignoli et al., "Isolation, Characterization, and Transduction of Endometrial Decidual Tissue Multipotent Mesenchymal Stromal/Stem Cells from Menstrual Blood," BioMed Research International, vol. 2013, Article ID 901821, 2013, 14 pages (plus cover sheet at end).
Yang et al., "Proteomic Analysis of Menstrual Blood," The American Society of Biochemistry and Molecular Biology, Inc., Molecular & Cellular Proteomics, vol. 11, No. 10, Jul. 20, 2012, pp. 1024-1035.
Warren et al., "Menstrual Effluent: A Tool for Better Understanding Endometriosis," Abstract only, Database Embase (online), Elsevier Science Publishers, Amsterdam, Netherlands, Database Accession No. EMB-621267524, Mar. 1, 2018, 2 pages.
EPO Communication Pursuant to Article 94(3) EPC dated Sep. 19, 2024, issued in European Patent Application No. 19763950.3.
Gargett et al., "Endometrial Stem/Progenitor Cells: The First 10 Years," Human Reproduction Update, vol. 22, No. 2, 2016, Advanced Access publication on Nov. 9, 2015, pp. 137-163.

\* cited by examiner

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: primer directed to human ALDH1A1

<400> SEQUENCE: 1
ccaaagacat tgataaagcc ataa                                          24

<210> SEQ ID NO 2
<211> LENGTH: 19
<212> TYPE: DNA
<213> ORGANISM: Artificial Sequence
<220> FEATURE:
<223> OTHER INFORMATION: primer directed to human ALDH1A1

<400> SEQUENCE: 2
cacgccatag caattcacc                                                19
```

METHODS FOR DETECTING AND TREATING ENDOMETRIOSIS

CROSS-REFERENCE TO RELATED APPLICATIONS

This application is a U.S. national stage entry under 35 U.S.C. § 371 of PCT International Patent Application No. PCT/US2019/020868, filed Mar. 6, 2019, which claims the benefit of U.S. Provisional Application No. 62/639,112, filed Mar. 6, 2018, the contents of each of which are hereby incorporated by reference in their entirety.

BACKGROUND OF THE INVENTION

The disclosures of all publications, patents, patent application publications and books referred to in this application are hereby incorporated by reference in their entirety into the subject application to more fully describe the art to which the subject invention pertains.

Endometriosis is a chronic and underdiagnosed disease which affects 5-10% of women of childbearing age and is characterized by growth of endometrial-like tissue outside of the uterus, most often in the peritoneal cavity. Delay in diagnosis is a major problem for management of this disorder, and treatment is often not initiated until the disease has progressed for many years. Although the exact etiology of endometriosis remains unknown, retrograde menstruation is recognized as a common underlying factor leading to the deposit of menstrual effluent (ME) into the peritoneal cavity. Differences in the cellular biology and genetics of the cells within ME are therefore likely to explain why endometriosis develops in only a subset of women. In addition, invasive diagnostic techniques are not preferred by patients.

The present invention addresses these needs and provides methods of noninvasively detecting and treating endometriosis.

SUMMARY OF THE INVENTION

Herein is provided a method of non-invasively diagnosing endometriosis in a subject comprising maintaining or culturing stromal cells, obtained from a menstrual effluent or discharge sample from the subject, under conditions permitting decidualization, quantifying a rate or extent of decidualization of the stromal cell, and comparing the rate of decidualization to a control value of decidualization indicative of a subject without endometriosis, wherein a rate or extent of decidualization of the stromal cell which is less than that of the control value of decidualization indicates that the subject has endometriosis.

Also provided a method of non-invasively diagnosing endometriosis in a subject comprising maintaining stromal cells obtained from a menstrual effluent or discharge sample from the subject, under conditions permitting decidualization, quantifying a rate or extent of decidualization of the stromal cell, and comparing the rate of decidualization to a control value of decidualization indicative of a subject without endometriosis, wherein a rate or extent of decidualization of the stromal cell which is less than that of the control value of decidualization indicates that the subject has endometriosis. In embodiments, the cells have been obtained less than 1 hour, 2 hours, 4 hours or 6 hours prior to quantifying the rate of decidualization.

Also provided a method of non-invasively diagnosing fertility in a subject comprising maintaining or culturing stromal cells, obtained from a menstrual effluent or discharge sample from the subject, under conditions permitting decidualization, quantifying a rate or extent of decidualization of the stromal cell, and comparing the rate of decidualization to a control value of decidualization indicative of a subject who is fertile, wherein a rate or extent of decidualization of the stromal cell which is less than that of the control value of decidualization indicates that the subject has infertility.

Also provided is a method of non-invasively diagnosing endometriosis in a subject comprising quantitating expression of one or more proteins in a stromal cell obtained from a menstrual discharge sample from the subject and comparing the expression quantitated to a control value of expression of the one or more protein indicative of a subject without endometriosis, wherein an amount of expression quantitated less than the control value indicates that the subject has endometriosis.

Also provided is a method of non-invasively diagnosing endometriosis in a subject comprising quantitating a protein modifications (e.g., phosphorylation), a gene expression, mRNA or microRNA levels, or an epigenetic change (e.g. DNA methylation, histone modification, or altered chromosomal state) obtained from a menstrual discharge sample from the subject and comparing the expression quantitated to a control value of expression of the same indicator in a subject without endometriosis, wherein an amount of the indicator quantitated less or more than, as appropriate, than the control value indicates that the subject has endometriosis.

Also provided is a kit for non-invasively diagnosing endometriosis in a subject comprising a cup for collection of menstrual effluent stromal cell, an amount of cAMP for effecting stromal cell decidualization, and an amount of 17-beta estradiol and/or medroxyprogesterone for effecting stromal cell decidualization.

Also provided is a kit for non-invasively diagnosing endometriosis in a subject comprising a menstrual cup or polyether polyurethane menstrual sponge, either intravaginally or as an external collection device, for collection of menstrual effluent. The kit provides for methods of recovery of stromal cells from sponge devices using trypsinization followed by culture of recovered stromal cells, using an amount of 8-bromoadenosine 3',5'-cyclic monophosphate (cAMP) for effecting stromal cell decidualization under low serum conditions, and an amount of 17-beta estradiol and/or medroxyprogesterone for effecting stromal cell decidualization.

Also provided is a method of treating endometriosis in a subject comprising obtaining an identification of the subject as in need of treatment of endometriosis, wherein the subject has been identified as having endometriosis by a method described herein, and treating the subject by performing a laproscopic surgery with excision or ablation of endometriosis lesions, or hysterectomy, or administering an amount of a progestin, a gonadotropin-releasing hormone agonist or a birth control pill effective to treat endometriosis.

Also provided is a method of identifying patients at risk for endometriosis by identifying subclinical inflammation of the uterine lining (e.g. chronic endometritis).

Also provided is a method of preventing the progression or development of endometriosis in a subject by administration of an inhibitors of a pro-inflammatory cytokine (such as TNFα, and IL-1β), or by administration of a compound that attenuates a cellular effect of a cytokines on decidualization and/or proliferation capacity of uterine stromal fibroblast cells (SFCs).

BRIEF DESCRIPTION OF THE FIGURES

FIG. 4A-4B: Transient exposure of SFCs to inflammatory cytokines (TNFα (shown) or IL-1β (not shown)) leads to persistent defects in SFC decidualization capacity.

DETAILED DESCRIPTION OF THE INVENTION

List of abbreviations: ALDH1A1, aldehyde dehydrogenase 1 family member A1; 17-beta estradiol, E2; 8-Bromoadenosine 3',5'-cyclic monophosphate, cAMP; insulin growth factor binding protein-1, IGFBP-1; medroxyprogesterone acetate, MPA; menstrual effluent, ME; mesenchymal stem cells, MSCs; paraformaldehyde, PFA; podoplanin, PDPN; stromal fibroblast cells, SFCs.

A method of non-invasively diagnosing endometriosis in a subject comprising maintaining a stromal cell, obtained from a menstrual discharge sample from the subject, under low serum conditions permitting decidualization, quantifying a rate or extent of decidualization of the stromal cell, and comparing the rate of decidualization to a control value of decidualization indicative of a subject without endometriosis, wherein a rate or extent of decidualization of the stromal cell which is less than that of the control value of decidualization indicates that the subject has endometriosis. Low serum as used herein means a concentration of 3% serum or less. In embodiments, the serum is at a level of 2% or less.

In embodiments, the menstrual discharge sample comprises menstrual blood. In embodiments, the method further comprises obtaining the menstrual discharge sample from the subject.

In embodiments, the stromal cell is contacted with 8-Br-cAMP and one or more hormones to effect decidualization.

In embodiments, the one or more hormones comprise 17-beta estradiol and/or medroxyprogesterone.

In embodiments, the rate or extent of decidualization is quantified by measuring IGFBP-1 protein production, IGFBP1 mRNA expression, or changes in cell morphology by the stromal cell.

In embodiments, ALDH1A1 expression, or ALDH1A1 mRNA levels, are quantified.

In embodiments, the stromal cell is a stromal fibroblast cell (SFC).

In embodiments, the SFC is identified as being an SFC by being identified as being: CD34−/CD45−/CD326−/CD31−/CD90+/CD105+/CD73+.

In embodiments, the SFC is CD140b+/CD13+CD29+/CD44+/CD49f+.

A method of non-invasively diagnosing endometriosis in a subject comprising quantitating expression of one or more proteins in a stromal cell obtained from a menstrual discharge sample from the subject and comparing the expression quantitated to a control value of expression of the one or more protein indicative of a subject without endometriosis, wherein an amount of expression quantitated less than the control value indicates that the subject has endometriosis.

In embodiments, quantitating the one or more proteins comprises quantitating ALDH1A1 expression.

A method of non-invasively diagnosing endometriosis in a subject comprising quantitating a level of ALDH1A1 mRNA in a stromal cell obtained from a menstrual discharge sample from the subject and comparing the level quantitated to a control value of ALDH1A1 mRNA indicative of a subject without endometriosis, wherein an amount of ALDH1A1 mRNA quantitated less than the control value indicates that the subject has endometriosis. In embodiments, the stromal cell is a stromal fibroblast cell (SFC).

In embodiments, quantitating the one or more proteins comprises is performed indirectly by measuring a protein-encoding RNA level, for example ALDH1A1 gene expression is determined by measuring mRNA.

A kit for non-invasively diagnosing endometriosis in a subject comprising a menstrual cup or polyether polyurethane menstrual sponge for collection of menstrual effluent comprising a stromal cell, an amount of cAMP for effecting stromal cell decidualization, and an amount of 17-beta estradiol and/or medroxyprogesterone for effecting stromal cell decidualization and culturing stromal cells. In an embodiment, the stromal cells are cultured in DMEM containing 2% fetal bovine serum.

In embodiments, the cAMP is 8-Br-cAMP.

In embodiments, the kit further comprises one or more reagents for the culture of stromal fibroblast cells.

In embodiments, the kit further comprises one or more reagents for measurement of IGFBP-1 concentrations in supernatant of cultured stromal fibroblast cells by ELISA.

In embodiments, the kit further comprises one or more reagents in order to measure morphological changes of SFCs that quantitatively reflect decidualization capacity.

A method of treating endometriosis in a subject comprising obtaining an identification of the subject as in need of treatment of endometriosis, wherein the subject has been identified as having endometriosis by a method described herein, and treating the subject by performing a laroposcopic surgery with excision or ablation of endometrial lesions or hysterectomy, or administering an amount of a progestin, a gonadotropin-releasing hormone agonist or a birth control pill effective to treat endometriosis.

A method of treating and or preventing endometriosis in a subject identified as at risk for endometriosis by the methods described herein and administering to the subject locally or systemically an anti-inflammatory agent that targets a cytokine. In embodiments, the cytokines are TNFalpha and/or IL 1beta. Anti-inflammatory agents directed to cytokine(s) are known in the art, including certain organic small molecules (see, e.g. www.ncbi.nlm.nih.gov/pmc/articles/PMC3752337/, incorporated by reference; anticytokines may also be biologics, e.g. monoclonal antibodies or fusion proteins directed against a known cytokine such as TNFalpha or IL-1beta).

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Patients with and without endometriosis were consented to provide ME. ME was analyzed by flow cytometry for CD45− and CD45+ cell populations or used to isolate stromal fibroblast cells. ME-derived stromal fibroblast cells were assessed using decidualization assays following the addition of cAMP and IGFBP-1 concentrations in the culture supernatants were measured by ELISA. In addition, RNA was collected and analyzed by RNA-Seq and qPCR for markers of decidualization and to identify differentially expressed genes in ME-derived stromal fibroblast cells obtained from controls and subjects with endometriosis (±cAMP).

Results: Flow cytometry analysis of cell subsets within the CD45+ fraction of ME revealed a significant decrease in the number of uterine NK cells in endometriosis patients compared with controls ($p<0.01$). No other significant differences within either the CD45+ or CD45− cell populations were observed. Most strikingly, ME-derived stromal fibroblast cells cultured from endometriosis subjects showed impaired decidualization potential compared with controls.

Highly significant differences in decidualization response were detected by measuring IGFBP-1 production at multiple time points after cAMP stimulation ($p=0.0025$ at 6 hrs; $p=0.0045$ at 24 hrs; $p=0.0125$ at 48 hrs). RNA-Seq and qPCR analyses were used to identify genes differentially expressed by ME-derived stromal fibroblast cells obtained from endometriosis and control subjects.

Highly significant differences in decidualization response can also be detected by morphological changes observed in live cells (SFC) at 24 to 48 hours.

Subject Recruitment and Enrollment—Endometriosis subjects were recruited through the Research OutSmarts Endometriosis (ROSE) study (see world wide web at feinsteininstitute.org/rose-research-outsmarts-endometriosis/; IRB #13-376A) and control subjects were recruited from the Genotype and Phenotype (GaP) registry (see world wide web at feinsteininstitute.org/robert-s-boas-center-for-genomics-and-humangenetics/gap-registry/; IRB #13-627A); both studies were approved by the Institutional Review Board (IRB) of Northwell Health. Briefly, women of reproductive age who were not pregnant or breast-feeding, did not use an internal birth control device (e.g. IUD) and were menstruating and willing to provide ME sample(s) were recruited and consented. Women who reported the diagnosis of endometriosis, as determined by laparoscopic surgery and were at least one year post-op following endometrial lesion removal, were recruited via the ROSE study (22 to 43 years old). Control subjects who self-reported no history suggestive of a diagnosis of endometriosis were recruited through the GaP registry (21 to 47 years old). For functional decidualization experiments using ME from endometriosis patients and controls, only subjects who reported that they were not using hormonal birth control were included.

Collection of menstrual effluent (ME)—ME was collected for up to 6-10 hrs per collection on days 0, 1, or 2 of the menstrual phase when flow is the heaviest, where day 0 is the first day of the menstrual cycle, using the DivaCup (a menstrual cup produced by Diva International Inc., Ontario, Canada) as described previously [25] or using a soft internal menstrual sponge (Gynotex), or external sponge placed on a menstrual pad. ME from menstrual cups was transferred to a sterile 50 mL conical tube containing 1 mg Normocin™ (Invivogen, San Diego, CA) and 500 units penicillin streptomycin (Gibco), placed in a refrigerated box and transported by express shipment to the lab within approximately 24 hrs. ME-containing menstrual sponges were transferred into a sterile 50 ml collection cup containing 10 ml sterile saline containing 2.5 mg Normocin™ and 1000 units penicillin streptomycin (Gibco). In pilot experiments no differences were observed in freshly obtained ME vs. 24 hr refrigerated/shipped ME, based on cellular composition determined by flow cytometry, viability of non-CD66+ cells by flow cytometry, or isolation/culture success of ME-derived SFCs. These observations are consistent with those of van der Molen and colleagues, who reported that CD45+/CD66− ME cells remained viable for at least 72 hr post collection [26]. Menstrual sponges were washed with PBS and trypsinized with Trypsin-EDTA (0.05%) to collect ME-cells. In pilot experiments no differences were observed in freshly obtained ME using a menstrual cup vs. soft menstrual sponge based on isolation/culture success/decidualization capacity of ME-derived SFCs.

Flow cytometry of ME and cultured SFCs—After removing the soluble fraction from whole ME following a brief centrifugation and lysis of red blood cells with BD Pharm Lyse (BD Biosciences, Billerica, MA), samples (from n=8 endometriosis and n=14 control subjects) were passed through a 35 μm cell strainer attached to polystyrene FACS tube (Thermo Fisher Scientific, Bridgewater, NJ). ME-cells were then pelleted and incubated with Human Fc Block (BD Biosciences) for 20 min. After a brief wash, cells were incubated with either the CD45+ or CD45− panels of antibodies listed in Table 1 or the appropriate isotype control antibodies. All cells were subjected to Aqua live/dead viability staining (Thermo Fisher) and then stained with antibodies in Table 1 for 30 min at 4° C. The cells were washed twice with 1% FBS in PBS and fixed with 3% paraformaldehyde (PFA) if not being analyzed same day. All data were collected on the LSR II Flow Cytometer (BD) and analyzed using FlowJo software (version 10.1r5, Ashland, OR).

TABLE 1

FACS Staining Panels for fresh ME.

| Fluorochrome | Antigen | Cat. No |
|---|---|---|
| CD45+ Staining Panel | | |
| PE | CD20 | 555623 |
| FITC | CD16 | 302006 |
| APC | CD56 | 555518 |
| Pacific Blue | CD66b | 305112 |
| APC-Cy7 | CD3 | 557757 |
| PerCP-Cy5.5 | CD14 | 562692 |
| PE-Cy7 | CD45 | 557748 |
| CD45− Staining Panel | | |
| PE | CD105 | 560839 |
| PerCP-Cy5.5 | CD326 | 347199 |
| APC | CD73 | 560847 |
| FITC | CD90 | 555595 |
| APC-Cy7 | CD31 | 563653 |
| PE-Cy7 | CD45 | 557748 |
| Aqua (AmCyan) | Live/Dead | L34966 |
| CD45+ Staining Panel Isotype Controls | | |
| PE | Mouse IgG$_{2b}$, κ | 555743 |
| FITC | Mouse IgG$_1$ | 349041 |
| APC | Mouse IgG$_1$, κ | 555751 |
| Pacific Blue | Mouse IgM, K | 401619 |
| APC-Cy7 | Mouse IgG1, K | 557873 |
| PerCP-Cy5.5 | Mouse IgG2b, K | 558304 |
| PE-Cy7 | Mouse IgG$_1$ | 348798 |
| CD45− Staining Panel Isotype controls | | |
| PE | Mouse IgG$_1$ | 349043 |
| APC | Mouse IgG$_1$, κ | 555751 |
| PerCP-Cy5.5 | Mouse IgG$_1$, κ | 552834 |
| FITC | Mouse IgG$_1$ | 349041 |
| APC-Cy7 | Mouse IgG1, K | 557873 |
| PE-Cy7 | Mouse IgG$_1$ | 348798 |

For in-depth profiling, cultured SFCs (passage 2 from n=6 endometriosis and n=5 control subjects), as described below, were lifted with ACCUTASE™ (STEMCELL TECHNOLOGIES, Cambridge, MA) at confluence and resuspended in Brilliant Stain Buffer (BD Biosciences) with the staining antibody panels listed in Table 3 or appropriate isotype control antibodies for 30 min at 4° C., washed twice with 1% FBS in PBS, and fixed with 2% PFA. All data were collected on the LSR II Flow Cytometer (BD) and analyzed using FlowJo software (version 10.1r5; Ashland, OR).

TABLE 2

ME-SFC Staining Panels

| Fluorochrome | Antigen | Company | Cat. No. |
|---|---|---|---|
| PERCP-Cy5.5 | CD105 | BD Pharmingen | 560819 |
| Brilliant violet 510 | CD90 | BioLegend | 328125 |
| Brilliant violet 421 | CD73 | BioLegend | 344007 |
| APC | CD140b | BioLegend | 323608 |
| Brilliant violet 711 | CD44 | BioLegend | 103057 |
| PE-Cy7 | Podoplanin | BioLegend | 337013 |
| PE | CD49f | BioLegend | 313611 |
| PERCP-Cy5.5 | Isotype | BD Pharmingen | 552834 |
| Brilliant violet 510 | Isotype | BioLegend | 400171 |
| Brilliant violet 421 | Isotype | BioLegend | 400157 |
| APC | Isotype | BioLegend | 400121 |
| Brilliant violet 711 | Isotype | BioLegend | 400653 |
| PE-Cy7 | Isotype | BioLegend | 400521 |
| PE | Isotype | BioLegend | 400507 |

ME-derived stromal fibroblast cell (SFC) isolation and culture—Whole ME (500 μL-1000 μL) was plated in T75 flasks in SFC media: 10% FBS (MSC-qualified, Gibco), 1× glutamine (Gibco), 100 units/ml penicillin-streptomycin (Gibco), and 100 μg/ml Normocin™ in DMEM (Gibco). Flasks were incubated at 37° C./5% CO2 for 48-72 hrs in order to isolate SFCs by adherence. After washing, adherent cells (passage 0, p0) were cultured to 80%-90% confluence before lifting with trypsin/EDTA, subculturing after a 1:6 dilution, and subsequently freezing stock cells at passage 1 (p1).

Decidualization Assays Using ME-derived SFCs—Fresh or cryopreserved ME-derived SFCs (p0, p1 or p2)) were defrosted and plated in 24-well plates in SFC media; at confluence SFCs were incubated at 37° C./5% CO2 in decidualization media (2% FBS MSC-qualified, 1λ glutamine, 100 units/ml penicillin-streptomycin, and 100 ug/ml Normocin™ in Phenol Red Free DMEM with either 0.5 mM 8-Bromoadenosine 3′,5′-cyclic monophosphate (cAMP, Sigma-Aldrich, St. Louis, MO)±10 nM 17-beta estradiol (E2) (Tocris, Minneapolis, MN) and 1 μM medroxyprogesterone acetate (MPA, Sigma-Aldrich) or vehicle (PBS for studies with cAMP alone or 0.01% ethanol for studies with cAMP+E2+MPA). Cells were stimulated for 6 hrs, 24 hrs, and 48 hrs, at which point supernatants and cell lysates were collected from each well for the time course experiment. Supernatants were analyzed for IGFBP-1 concentrations by ELISA (Duoset, R&D Systems, Minneapolis, MN) and results were normalized to cell lysate protein concentrations using the Bio-Rad Protein Assay Kit (Bio-Rad, Hercules, CA). Alternatively, results are normalized to cell number as observed by live cell counting in cell culture wells.

RNA-Seq and qPCR—Total cellular RNA was isolated following stimulation of ME-derived SFCs (collected from n=7 endometriosis subjects and n=7 control subjects) with either 0.5 mM cAMP or vehicle for 6 hrs, as described above using the mirVana™ miRNA Isolation Kit and treated with the DNAfree™ kit (Ambion) to remove DNA (Ambion). Supernatants were also collected and analyzed for IGFPB-1 by ELISA, as described above. RNA sequencing was performed using the Illumina mRNA TrueSeq Stranded method. The raw image files from the NextSeq sequencer were demultiplexed and converted to FASTQ files using Illumina's bcl2fastq BaseSpace App. The FASTQ files were aligned to the hg19 human reference genome from GENCODE using the STAR2 aligner and the digital gene counts quantified using HTSeq. The differential expression analysis was done using DESeq2.

ALDH1A1 expression was assessed by qPCR using RNA collected from ME-SFCs following 6 hr treatment with vehicle or 0.5 mM cAMP (n=7 endometriosis subjects and n=7 control subjects). qPCR was performed with probes and primers designed using ProbeFinder online software (left primer: ccaaagacattgataaagccataa (SEQ ID NO:1); right primer: cacgccatagcaattcacc (SEQ ID NO:2)) and probe #82 of the Universal ProbeLibrary (Roche, Basel, Switzerland). qPCR, using GAPDH as control, was performed on the Roche LightCycler 480 qPCR machine using the following conditions: 2 min at 50° C., 10 min at 95° C., followed by 40 cycles of 15 seconds at 95° C. and 1 min at 60° C. Relative changes in gene expression were calculated as fold-changes using the comparative Ct (ΔΔCt method) and statistical analysis was done through the Mann-Whitney Test [27]. ALDH1A1 expression differences are dependent on serum concentrations.

In vitro exposure of ME-SFCs to inflammatory cytokines (e.g. TNFα) reduces decidualization capacity. Acute exposure: ME-SFCs (p1) were plated in 96-well plates in DMEM 10% FBS pen-strep-glutamine and treated with either vehicle or TNFα (1 pg/ml-10 ng/ml); 24 hrs later the media was replaced with DMEM 2% FBS pen-strep-glutamine and ME-SFCs were treated with vehicle of cAMP (0.5 mM) to induce decidualization. After 24 hrs, culture supernatants were collected and IGFBP-1 protein levels were measured by ELISA. Long-term studies: ME-SFCs (p1-p2) were plated in T25 flasks in DMEM 10% FBS, pen-strep-glutamine and treated with either vehicle or TNFα (0.1 ng/ml-1.0 ng/ml) on days 0 and 5; ME-SFCs were subcultured as needed and on day 30 ME-SFCs were trypsinized and plated in DMEM 2% FBS pen-strep-glutamine and treated with vehicle or cAMP (0.5 mM) (25 days after the final TNFα treatment). Twenty four hours later, the culture supernatants were collected and IGFBP-1 protein levels were measured by ELISA.

Statistical Analyses—Flow cytometry analyses of the cellular composition of whole ME: All analyses were carried out separately for each cell population. For each cell population within the CD45+ and CD45− subsets, a linear mixed model was used to examine the association between group and that population using SAS Version 9.4 (SAS Institute Inc., Cary, NC). The mixed models approach was used to account for the hierarchical nature of the data (namely, multiple samples from one or more cycles within a subject). Time of day (evening, overnight) and day of cycle collection was started (0, 1-2) were included as covariates in the model to adjust for any effects they might have on cell population.

Transformations (namely log or arcsine square root) were used to better meet the assumptions of the linear model. However, as the results obtained from the models using transformed data did not differ qualitatively from those using the raw data, results using the raw data are presented for ease of interpretation.

SFC Decidualization Time Course: To determine differences in IGBFP-1 protein levels between treatments and cases/controls, a Bayesian hierarchical model was implemented. The data consists of normalized measurements of IGFBP-1 protein levels of 7 endometriosis cases and 7 controls, across four different treatments (cAMP, vehicle for cAMP alone, ethanol vehicle, and cAMP+MPA+E2). Each treatment has protein measurements for all the subjects at three different time points (6 hrs, 24 hrs, and 48 hrs).

The response variable—protein levels—was log-transformed in order to adjust for heteroscedasticity in the original scale and the covariate included was an indicator variable for whether a subject was a case or a control, and indexed according to the treatment and time period in which the subjects were analyzed. For the hierarchical structure, subjects were nested within treatments at each time point. A model assuming normally distributed residuals estimated both the mean protein content at each level; a group parameter was used to estimate the effect of being in the case/control group. The posterior probability of the group effect being zero was assessed. Data was arranged using R (version 3.3.2) and the model was implemented in Stan (version 2.16.2) using the R interface. The model is estimated using the No-U-Turn sampler algorithm [28] a version of Hamiltonian Monte Carlo [29]. Once posterior draws were estimated, the model was simulated for each draw, resulting in the generated quantities. All other data were analyzed using the Mann-Whitney test.

Results

ME Contains CD45+ and CD45− Cell Populations and ME Collected from Endometriosis—Subjects Has Fewer Uterine NK Cells: Flow cytometric analysis was performed on fresh ME collected from control and endometriosis subjects for endometriosis and control subjects CD45+ (n=14 control, n=8 endometriosis) and CD45− (n=14 control, n=6 endometriosis). Box plots were constructed from the cellular composition CD45+ subsets (CD66b+ granulocytes [Granulo], CD14+ monocytes [Mono], CD20+ B cells, CD3+ T cells, and CD56+ uterine natural killer (uNK) cells) (C) and CD45− subsets (CD45− CD326+ epithelial cells [Epith], CD31+ endothelial cells [Endo], CD326−/CD31− cells, and CD73+/CD90+/CD105+ [SFCs] (D) found in menstrual effluent from women with and without endometriosis. The CD66b+ and CD66b− populations were normalized to the CD45+ population cell counts and the CD14+ Mono, CD20+ B Cells, CD3+ T cells, and CD56+ uNK cell populations were normalized to the CD66b-population cell counts. The Epith, Endo, CD326−/CD31− cells, and SFC populations were normalized to the CD45− population cell counts.

The results showed, after gating out dead cells, ME is mainly comprised of CD45+ cells, with the CD45-cell populations contributing on average 1.6±0.3% for control subjects and 1.9±0.5% for endometriosis subjects. The CD45+ population includes granulocytes, monocytes, T cells, B cells, and natural killer (NK) cells. The vast majority of NK cells found in ME are uterine NK (uNK) cells based on their lack of CD16 expression and high expression of CD56. Depending on the ME sample the CD66b+ population made up the majority of the CD45+ population, with 55.6±5.1% for control subjects and 56.7±6.5% for endometriosis subjects. The CD66b+ granulocyte population was variable between subjects and samples collected, possibly due to the poor viability of granulocytes. In order to account for the variability of the granulocyte population between samples, the data was normalized by adjusting the cell count of the population of interest (monocytes, T cells, B cells, or uNK cells) to the cell count of the CD45+ CD66b− population.

Although, no significant differences between ME collected from endometriosis vs. control subjects were found for granulocytes, monocytes, T cells, or B cells, there were significantly less uNK cells (p=0.01) in ME collected from endometriosis subjects compared to control subjects.

The CD45− populations analyzed included epithelial cells, endothelial cells, and stromal fibroblast cells (SFCs). There were no significant differences found in the percentages of epithelial cells (CD31−, CD326+/EPCAM) or endothelial cells (CD31+, CD326−) among total CD45− cells when comparing ME obtained from control to endometriosis subjects. The SFC population was defined as: CD45−/CD326−/CD31−/CD90+/CD105+/CD73+ and no significant differences in the SFC populations were found when comparing fresh ME obtained from endometriosis subjects to control subjects.

Figure 3:
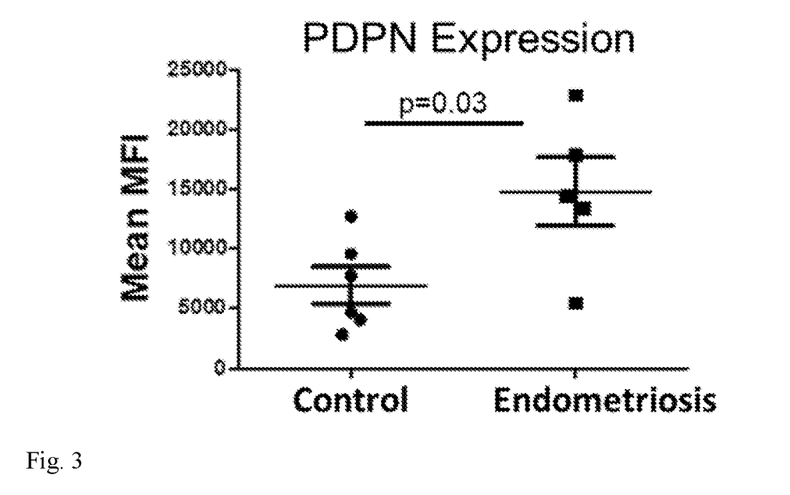
FIG. 3: Surface expression of podoplanin (PDPN) by ME-SFCs obtained from endometriosis subjects and controls. Plots show average genometric mean fluorometric intensity (MFI) for PDPN surface expression by subjects with (Endo, n=5 subjects) vs. without (Control, n=6 subjects), as determined by flow cytometry. *p=0.03, calculated using Mann Whitney Test. ME-SFCs obtained from healthy controls (n=6) or endometriosis subjects (n=5) were grown to confluence in DMEM containing 10% FBS, pen-strep-glutamine. ME-SFCs were harvested using non-enzymatic Accutase solution. Cells were washed and analyzed by flow cytometry using either PE/Cy7-labeled anti-PDPN antibody (BioLegend, Cat #337013, clone NC-08) or PE/Cy7-labeled isotype control (BioLegend, Cat #400125). Data are shown as geometric mean fluorescence intensity (MFI) for each subjects' ME-SFCs; horizontal lines are the group means. P=0.03 calculated using the Mann Whitney Test.

Next, cultured ME-derived SFCs (p1) were assessed for surface markers by flow cytometry. Cultured ME-derived SFCs express CD73, CD90, CD105, and CD140b but not CD45 or CD326. Flow cytometry gating of cultured ME-derived SFCs showed a CD45-CD326-population. The CD45− population of ME derived SFCs from endometriosis (n=7) and control (n=7) subjects at passage 1 were further analyzed by flow cytometry for CD90, CD73, CD140b, and CD105 expression. CD105 expression is lower on endometriosis-SFCs when compared to control subject-SFCs. In addition, ME-SFCs expressed the fibroblast marker CD140b, as well as other markers found on stromal cells (Table 2). No significant differences in CD90 or CD73 expression (based on geometric mean fluorescence intensity, gMFI) were found when comparing cultured ME-SFCs derived from endometriosis to control subjects. Of particular interest, PDPN expression (MFI) was significantly higher on endometriosis SFCs (n=5) than control SFCs (n=6) (p=0.03).

Figure 1:
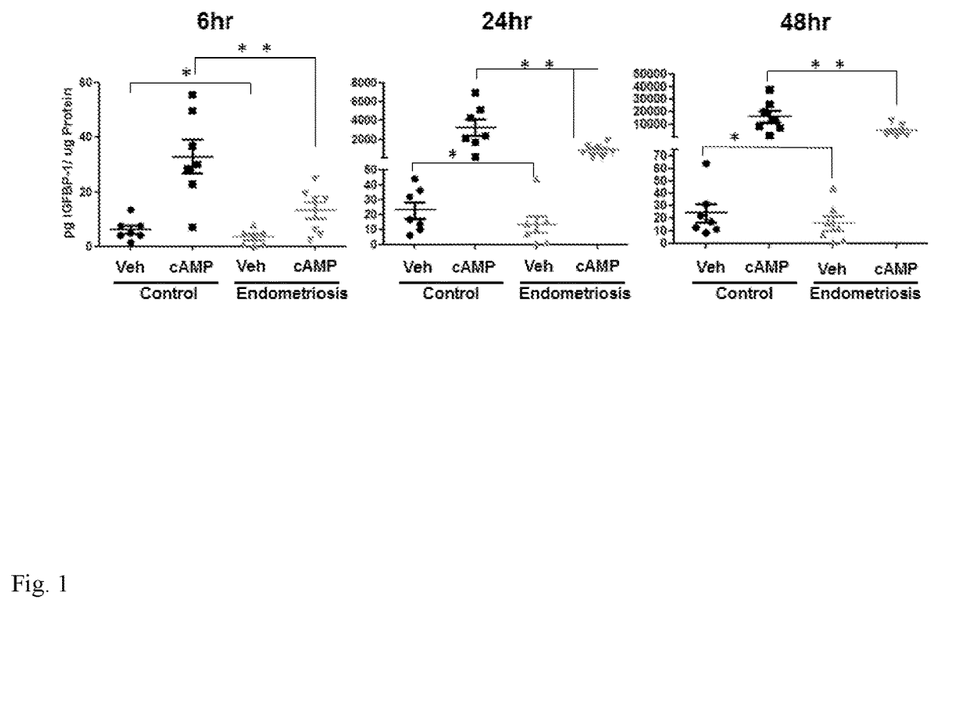
FIG. 1: ME-derived stromal fibroblast cells (SFCs) obtained from endometriosis subjects exhibit reduced decidualization capacity which persists until at least passage 2. Time course of IGFBP-1 secretion by vehicle and cAMP treated (0.5 mM) ME-derived SFCs isolated from endometriosis (Endo) and control subjects (n=7 control, n=7 endometriosis) in DMEM 2% fetal bovine serum. Data are shown as IGFBP-1 values for each subject's SFC culture and the horizontal lines represent group means. **posterior probabilities (Pr)<0.01 *Pr<0.05. Statistics were performed on log transformed data, as described in the methods.

Cultured ME-derived SFCs from Endometriosis Subjects Have Reduced Decidualization Capacity: It has been reported that endometrial stromal cells cultured from endometrial biopsies and hysterectomy samples obtained from endometriosis subjects have a reduced potential to decidualize when compared to those obtained from control subjects [12, 30]. In order to investigate whether similar differences are observed using cultured SFCs derived from ME, in vitro decidualization assays were performed at 3 different time points: 6 hrs, 24 hrs, and 48 hrs post 0.5 mM cAMP vs. vehicle using passage 2 SFCs obtained from control and endometriosis subjects. Decidualization was assessed by measuring IGFBP-1 concentrations in the culture supernatants by ELISA. As expected, stimulation with cAMP induced decidualization of MESFCs, as determined by enhanced IGFBP-1 production, which was detectable at 6 hrs and continued to increase through 48 hrs. Significantly less IGFBP-1 was produced following both vehicle-treatment and cAMP-treatment at all three time points by ME-SFCs obtained from endometriosis subjects when compared to control subjects (p<0.05). Similarly, the addition of MPA and E2 to cAMP induced decidualization, as determined by IGFBP-1 levels.

ME-SFCs obtained from endometriosis subjects produced significantly less IGFBP-1 following stimulation when compared to control ME-SFCs. Additionally, individual subject's ME-SFCs that produce high or low amounts of IGFBP-1 do so consistently across all three-time points. Cell morphologic changes were correlated with IGFBP1 production and thus also reflect dedidualization.

Gene Expression Analysis of Cultured ME-SFCs Derived From Endometriosis Subjects. RNA-Seq was performed on cultured ME-SFCs isolated from a small number of endometriosis (n=3) and control (n=3) subjects following cAMP or vehicle-treatment for 6 hrs. Many of the genes previously reported to be increased during decidualization were also increased in the decidualizing SFCs from both endometriosis subjects and controls. These genes included IGFBP1, SST, PRL, BCL2L11, WNT5A, and FOXO1. When comparing ME-SFCs obtained from endometriosis and control subjects, differentially regulated genes were observed in both vehicle-treated and cAMP-treated cultures.

Figure 2:
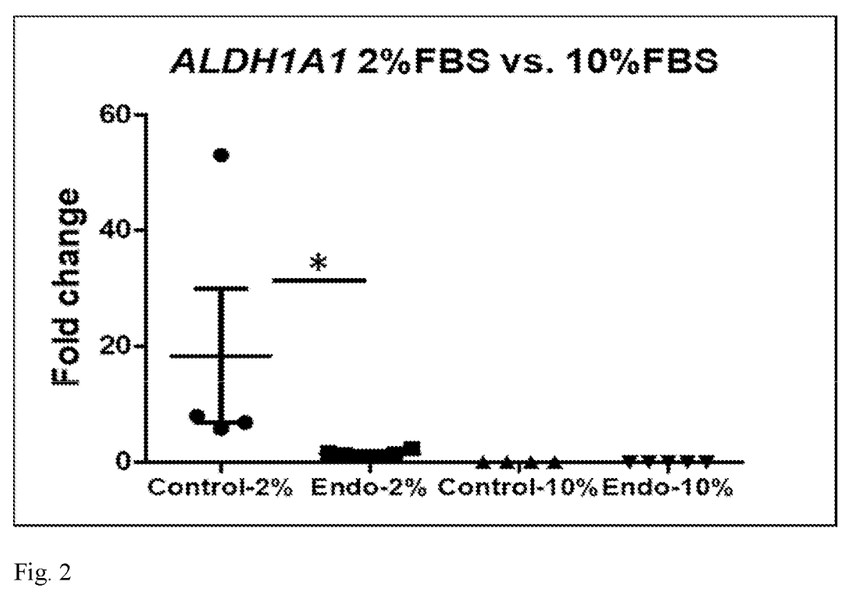
FIG. 2: Low serum conditions are required for observing changes in ALDH1A1 mRNA expression, thereby revealing differences between SFCs from controls and endometriosis subjects' ALDH1A1 expression and other transcripts under in vitro conditions of decidualization. ALDH1A1 mRNA expression by confluent ME-SFCs collected from controls (n=4 subjects) and endometriosis subjects (n=5 subjects) after 24 hrs in DMEM containing 2% FBS vs. DMEM 10% FBS. ALDH1A1 mRNA expression was analyzed by qPCR and normalized to GAPDH expression. Individual data points are show, with means as horizontal bars. *p<0.05 compared.

The most striking difference between the control and endometriosis SFCs was the high expression of ALDH1A1 (encoding aldehyde dehydrogenase 1 family member A1) in control SFCs, regardless of treatment. These findings were confirmed using qPCR for a larger number of ME-SFCs (n=7 subjects per group). These differences were unaffected by stimulation with cAMP. Although the relative lack of expression in the endometriosis SFCs remained significant, there was an outlier in the endometriosis group which was not readily explained by any particular subject characteristic. The reduction in ALDH1A1 mRNA expression requires a 24 hr culture period in DMEM 2% FBS (from standard 10% FBS culture conditions).

Figure 4A:
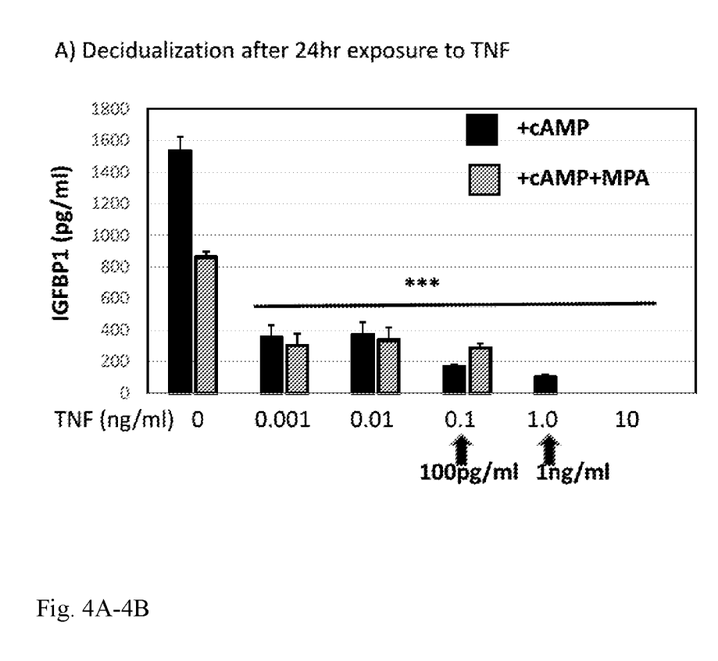
Figure 4B:
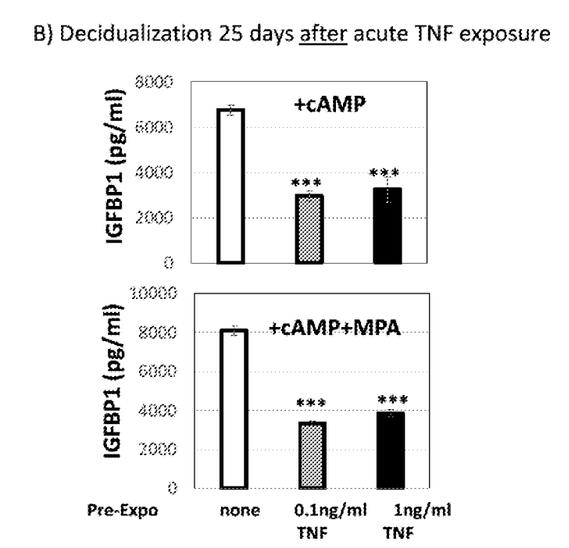

In vitro exposure to inflammatory cytokines such as TNF and IL1 reduces decidualization capacity acutely and this effect persists for up to 25 days, despite removal of TNF and multiple cell passages. Thus, short term exposure to TNF and/or IL1 leads to prolonged decidualization defects. In panel A, TNF alpha exposure at very low doses dramatically reduces decidualization capacity of SFCs from a normal (non-endometriosis) subject at 24 hours. Cell viability is not affected by these exposures (data not shown) and similar effects are observed with IL-1β (0.01-10 ng/ml) (data not shown). These results have been reported previously in the literature. However, it was also shown that these decidualization defects persist for at least 25 days after TNFα is removed from the culture with reductions in IGFBP1 production after decidualization with cAMP alone, or with cAMP and medroxyprogesterone. These data suggest that a permanent change in decidualization capacity of SFCs results from transient exposure to inflammatory cytokines.

Discussion

Almost all women experience retrograde menstruation, a process by which menstrual effluent (ME) shed from the endometrium is effluxed through the fallopian tubes into the peritoneal cavity, where it implants on the serosal surface [6]. Evidence that effluxed ME is likely to be a major source of cells responsible for the formation of peritoneal endometriosis lesions in patients is supported by studies in baboons showing that consecutive intraperitoneal injections of shed menses results in endometriosis lesions in the peritoneal cavity and by the presence of spontaneous endometriosis in menstruating non-human primates, along with the complete absence of endometriosis in non-menstruating mammals [16, 31, 32]. The findings suggest that analysis of ME shed from the endometrium can be harnessed to investigate the pathobiology of endometriosis and to develop early, non-invasive diagnostic methods for endometriosis.

Individual differences in the cellular content of ME offer a potential tool for investigating why only 5-10% of females actually develop endometriosis, given the ubiquity of retrograde menstruation. A relatively small number of published studies have analyzed the composition of ME, comparing it to that of peripheral blood; these studies primarily focused on phenotyping the CD45+ cell populations [26, 33]. Consistent with previous reports it was found that ME is mainly comprised of CD66b+ granulocytes, followed by CD3+ lymphocytes, CD56bright uNK cells, and then CD14+ monocytes and CD20+ B cells[26, 33]). The variability that observed among the various subpopulations of CD45+ cells was similar to that previously reported [26, 33]. Neither of these previous studies compared ME obtained from endometriosis subjects to controls. Despite the variability in the cellular composition of ME, it was found that endometriosis subjects had significantly lower percentages of uNK cells when compared to controls. uNK cells are CD56bright/CD16−, unlike peripheral blood NK cells which are CD56dim/CD16+. uNK cells are proposed to play an important role in endometrial vascularization and decidualization, as well as the development of decidualization-related infertility observed in women with endometriosis [22].

Decidualization is a process in which endometrial stromal fibroblast-like cells differentiate into specialized secretory decidual cells during the mid-secretory phase to prepare the uterus for implantation and placental development [22-24]. A very recent study reveals that uNK cells target and eliminate senescent endometrial stromal fibroblast-like cells, and this may be an important process for successful decidualization [34]. A reduction in uNK cells found in ME collected from subjects with endometriosis may be linked to the impaired elimination of senescent uterine cells that compromises the decidualization process—which is implicated in the infertility observed in patients with endometriosis. Future studies will focus on more detailed analyses of the NK cell population found in ME collected from controls and subjects with endometriosis.

Several previous studies have highlighted the regenerative capacity of ME-derived CD45-mesenchymal and stromal cells [17-21]. The CD45− cell fraction contributes to approximately 1.5-2% of the total non-RBC portion of ME. The majority of these cells were not endothelial or epithelial cells, but rather CD73/CD90/CD105 expressing cells. No significant differences were observed in these subpopulations of CD45− cells found in ME collected from endometriosis subjects vs. controls. However, this did not include a distinction between the endometrial MSC and SFC populations in the ME; this could be addressed in future studies using CD146/CD140b markers, as described by studies of endometrial biopsies [12]. Among cultured SFCs, we have observed a higher level of expression of podoplanin (PDPN) in stromal cells derived from patients with endometriosis. Podoplanin has been associated with increased proliferative and invasive capacity of fibroblasts populations and are expanded in the inflammatory lesions of rheumatoid arthritis. These data suggest that the phenotypic changes of SFCs observed in endometriosis patients may be functionally related to the proliferative and invasive behavior of intraperitoneal endometriotic lesions. ME A major innovation of this study over prior studies profiling the cellular composition of ME is that functional assessment of the SFCs (of the CD45− fraction) were included. Taking advantage of the fact that defects in stromal cell decidualization (obtained from invasive uterine biopsies) have been reported in the setting of endometriosis [30, 37, 38], ME-derived SFCs obtained from controls and endometriosis subjects were compared for their decidualization response using cAMP. It was demonstrated that a reduced decidualization response by ME-derived SFCs is clearly associated with endometriosis. In fact, ME-SFCs obtained from women with endometriosis exhibit significantly reduced IGFBP-1 expression in the absence of decidualization stimuli. These differences persist over time in culture and likely reflect a quantitative impairment in decidualization capacity, as well as a relative increase in proliferative capacity. This difference is observed with cAMP alone, as well as when decidualization is induced in the presence of cAMP+MPA+E2.

Interestingly, impaired decidualization capacity in control subjects' SFCs was occasionally observed. This may reflect the presence of asymptomatic endometriosis in these individuals. Alternatively, genetic variation may influence the decidualization response in the absence of endometriosis. Genetic differences play a significant role in risk for endometriosis; a recent meta-analysis of over 170,000 endometriosis patients and almost 200,000 controls revealed 14 genetic regions of interest, including WNT4, GREB1, ILIA, and CDKN2B [39]. The examination of phenotypic diversity of ME may also shed light on the mechanisms of genetic predisposition [40]. This of interest in decidualization capacity in control subjects who carry genetic risk alleles for endometriosis [40]. For example, WNT4 plays a direct role in the decidualization response, and WNT4 risk haplotypes for endometriosis have been reported to contain an estrogen response element that may regulate its expression [41].

A large registry of normal controls (GaP) with GWAS genotype data and subjects has been established for recall for phenotypic studies based on a genotype of interest [42, 43]. This offers the possibility of examining a variety of endometriosis risk haplotypes with regard to their impact on decidualization capacity in various populations. The use of ME as a source of SFCs makes such studies possible without the need for invasive procedures. One of the major benefits of this study is to open up the possibility of carrying out population-based genotype-phenotype studies that are relevant to better understanding the underlying pathogenesis of endometriosis. Another benefit of the invention, which permits sampling throughout menstruation and/or monthly, is informing the use of early, non-invasive diagnostic methods. The long delay between symptom onset and diagnosis in this disease is well established [3, 44], and no laboratory diagnostic makers have emerged to replace, or even guide, the performance of the gold standard of laparoscopic surgery and histologic confirmation. The expression of BCL6 [45] has been reported to be altered in secretory phase endometrial biopsies and may be useful diagnostically, but this approach will require invasive biopsy procedures. Other possible diagnostic markers for endometriosis include CA-125 [46], VEGF, microRNAs, immunologic markers, and soluble ICAM levels [47-55]. However, none of these can identify endometriosis patients with both high sensitivity and specificity. It is clear that the need for a non-invasive diagnostic marker or method remains, and that the analysis of ME provides this.

Although significant decidualization by ME-derived SFCs (based on IGFBP-1 protein release) was observed within 6 hr of cAMP simulation, and culturing ME is a usable method, a direct assessment of freshly isolated stromal cells from ME is most preferred based on gene expression, epigenetic analysis or other phenotypic changes in these cells. The fact that gene expression differences, such as ALDH1A1, can be observed in unstimulated cultured SFCs is significant.

This study is the first to demonstrate that uNK cells are significantly reduced in ME obtained from endometriosis subjects and that ME-derived SFCs from subjects with endometriosis exhibit significantly impaired decidualization, along with lower expression of ALDH1A1 than controls.

Decidualization defects may arise through many different genetic and environmental mechanisms, and these may suggest different approaches to therapy. Indeed it is possible that decidualization and gene expression changes defects in eutopic endometrium may in some cases arise as a result of the presence of endometriosis lesions in the peritoneum, as suggested by studies in the baboon [16]. In this context it will be of interest to study ME phenotypes before and after surgical or medical treatments and to correlate these findings with the presence or absence of persistent infertility. ME is particularly useful for these types of studies because it can be collected in a non-invasive manner repeatedly over several months.

In addition, the data herein indicate that chronic subclinical inflammation (increased TNFa or IL1) in the lining of the uterus (such as in chronic endometritis) may be an important factor that reduces decidualization capacity (and enhances proliferative capacity) of SFCs. This may be a common underlying factor in the predisposition to endometriosis, and infertility.

REFERENCES

1. Giudice L C. Clinical practice. Endometriosis. N Engl J Med. 2010. 362(25):2389-98.
2. Simoens S, Dunselman G, Dirksen C, Hummelshoj L, Bokor A, Brandes I, et al. The burden of endometriosis: costs and quality of life of women with endometriosis and treated in referral centres. Hum Reprod. 2012. 27(5): 1292-9.
3. Hadfield R, Mardon H, Barlow D, Kennedy S. Delay in the diagnosis of endometriosis: a survey of women from the USA and the UK. Hum Reprod. 1996. 11(4):878-80.

4. Ballard K, Lowton K, Wright J. What's the delay? A qualitative study of women's experiences of reaching a diagnosis of endometriosis. Fertil Steril. 2006. 86(5): 1296-301.
5. Giudice L C. Endometriosis. N Engl J Med. 2010. 362(25):2389-98.
6. Halme J, Hammond M G, Hulka J F, Raj S G, Talbert L M. Retrograde menstruation in healthy women and in patients with endometriosis. Obstet Gynecol. 1984. 64(2): 151-4.
7. Denu R A, Nemcek S, Bloom D D, Goodrich A D, Kim J, Mosher D F, et al. Fibroblasts and mesenchymal stromal/stem cells are phenotypically indistinguishable. Acta Haematol. 2016. 136(2):85-97.
8. Haniffa M A, Collin M P, Buckley C D, Dazzi F. Mesenchymal stem cells: the fibroblasts' new clothes? Haematologica. 2009. 94(2):258-63.
9. Hematti P. Mesenchymal stromal cells and fibroblasts: a case of mistaken identity? Cytotherapy. 2012. 14(5):516-21.
10. Ulrich C, Hart M L, Rolauffs B, Abele H, Gotze M, Benz K, et al. Mesenchymal stromal cells and fibroblasts. J Tissue Sci Eng 2012. 3(e109).
11. Figueira P G M, Abrão MS, Krikun G, Taylor H. Stem cells in endometrium and their role in the pathogenesis of endometriosis. Ann N Y Acad Sci. 2011. 1221(1):10-7.
12. Barragan F, Irwin J C, Balayan S, Erikson D W, Chen J C, Houshdaran S, et al. Human endometrial fibroblasts derived from mesenchymal progenitors inherit progesterone resistance and acquire an inflammatory phenotype in the endometrial niche in endometriosis. Biol Reprod. 2016. 94(5):118, 1-20.
13. Gargett C E. Identification and characterisation of human endometrial stem/progenitor cells. Aust N Z J Obstet Gynaecol. 2006. 46(3):250-3.
14. Masuda H, Matsuzaki Y, Hiratsu E, Ono M, Nagashima T, Kajitani T, et al. Stem cell-like properties of the endometrial side population: implication in endometrial regeneration. PLOS ONE. 2010. 5(4):e10387.
15. Gargett C E. Uterine stem cells: What is the evidence? Hum Reprod Update. 2007. 13.
16. Fazleabas A T, Brudney A, Gurates B, Chai D, Bulun S. A modified baboon model for endometriosis. Ann N Y Acad Sci. 2002. 955:308-17; discussion 40-2, 96-406.
17. Zhang Z, Wang J-a, Xu Y, Jiang Z, Wu R, Wang L, et al. Menstrual blood derived mesenchymal cells ameliorate cardiac fibrosis via inhibition of endothelial to mesenchymal transition in myocardial infarction. Int J Cardiol. 168(2):1711-4.
18. Meng X, Ichim T E, Zhong J, Rogers A, Yin Z, Jackson J, et al. Endometrial regenerative cells: A novel stem cell population. J Transl Med. 2007. 5(1):57.
19. Vu N B, Trinh V N-L, Phi L T, Phan N K, Van Pham P. Human menstrual blood-derived stem cell transplantation for acute hind limb ischemia treatment in mouse models. In: N. Bhattacharya and P. G. Stubblefield, Editors. Regenerative Medicine: Using Non-Fetal Sources of Stem Cells. London: Springer London; 2015. p. 205-15.
20. Borlongan C V K Y, Maki M, Yu S J, Ali M, Allickson J G, Sanberg C D, Kuzmin-Nichols N, Sanberg P R. Menstrual blood cells display stem cell-like phenotypic markers and exert neuroprotection following transplantation in experimental stroke. Stem Cells Dev. 19(4):439-52.
21. Rodrigues M C O, Lippert T, Nguyen H, Kaelber S, Sanberg P R, Borlongan C V. Menstrual blood-derived stem cells: in vitro and in vivo characterization of functional effects. In: F. Karimi-Busheri and M. Weinfeld, Editors. Biobanking and Cryopreservation of Stem Cells. Cham: Springer International Publishing; 2016. p. 111-21.
22. Gellersen B, Brosens J J. Cyclic decidualization of the human endometrium in reproductive health and failure. Endocr Rev. 2014. 35(6):851-905.
23. Dunn C L, Kelly R W, Critchley H O. Decidualization of the human endometrial stromal cell: an enigmatic transformation. Reprod Biomed Online. 2003. 7(2):151-61.
24. Ramathal C Y, Bagchi I C, Taylor R N, Bagchi M K. Endometrial decidualization: of mice and men. Semin Reprod Med. 2010. 28(1):17-26.
25. Howard C, Rose C L, Trouton K, Stamm H, Marentette D, Kirkpatrick N, et al. FLOW (finding lasting options for women): multicentre randomized controlled trial comparing tampons with menstrual cups. Can Fam Physician. 2011. 57(6):e208-15.
26. van der Molen R G, Schutten J H F, van Cranenbroek B, ter Meer M, Donckers J, Scholten R R, et al. Menstrual blood closely resembles the uterine immune microenvironment and is clearly distinct from peripheral blood. Hum Reprod. 2014. 29(2):303-14.
27. Cikos S, Koppel J. Transformation of real-time PCR fluorescence data to target gene quantity. Anal Biochem. 2009. 384(1):1-10.
28. Hoffman M D, Gelman A. The No-U-turn sampler: adaptively setting path lengths in Hamiltonian Monte Carlo. J Mach Learn Res. 2014. 15(1):1593-623.
29. Neal R M. An improved acceptance procedure for the hybrid monte carlo algorithm. J Comput Phys. 1994. 111(1):194-203.
30. Klemmt P A B, Carver J G, Kennedy S H, Koninckx P R, Mardon H J. Stromal cells from endometriotic lesions and endometrium from women with endometriosis have reduced decidualization capacity. Fertil Steril. 85(3):564-72. 31. D'Hooghe T M, Bambra C S, Suleman M A, Dunselman G A, Evers H L, Koninckx P R. Development of a model of retrograde menstruation in baboons (*Papio anubis*). Fertil Steril. 1994. 62(3):635-8.
32. D'Hooghe T M, Kyama C M, Chai D, Fassbender A, Vodolazkaia A, Bokor A, et al. Nonhuman primate models for translational research in endometriosis. Reprod Sci. 2009. 16(2):152-61.
33. Hosseini S, Shokri F, Tokhmechy R, Savadi-Shiraz E, Jeddi-Tehrani M, Rahbari M, et al. Menstrual blood contains immune cells with inflammatory and anti-inflammatory properties. Journal of Obstetrics and Gynaecology Research. 2015. 41(11):1803-12.
34. Brighton P J, Maruyama Y, Fishwick K, Vrljicak P, Tewary S, Fujihara R, et al. Clearance of senescent decidual cells by uterine natural killer cells in cycling human endometrium. Elife. 2017. 6.
35. Guerrero-Esteo M, Sanchez-Elsner T, Letamendia A, Bernabeu C. Extracellular and cytoplasmic domains of endoglin interact with the transforming growth factor-beta receptors I and II. J Biol Chem. 2002. 277(32):29197-209.
36. Hayrabedyan S, Kyurkchiev S, Kehayov I. Endoglin (cd105) and S100A13 as markers of active angiogenesis in endometriosis. Reprod Biol. 2005. 5(1):51-67.
37. Aghajanova L, Tatsumi K, Horcajadas J A, Zamah A M, Esteban F J, Herndon C N, et al. Unique transcriptome, pathways, and networks in the human endometrial fibroblast response to progesterone in endometriosis. Biol Reprod. 2011. 84(4):801-15.
38. Yin X, Pavone M E, Lu Z, Wei J, Kim J J. Increased activation of the PI3K/AKT pathway compromises decidualization of stromal cells from endometriosis. J Clin Endocrinol Metab. 2012. 97(1):E35-E43.
39. Sapkota Y, Steinthorsdottir V, Morris A P, Fassbender A, Rahmioglu N, De Vivo I, et al. Meta-analysis identifies five novel loci associated with endometriosis highlighting key genes involved in hormone metabolism. Nat Commun. 2017. 8:15539. 40. Rahmioglu N, Montgomery G W, Zondervan K T. Genetics of endometriosis. Womens Health (Lond). 2015. 11(5):577-86.
41. Zhang G, Feenstra B, Bacelis J, Liu X, Muglia L M, Juodakis J, et al. Genetic associations with gestational duration and spontaneous preterm birth. N Engl J Med 2017. 377(12):1156-67.
42. Gregersen P K. Closing the gap between genotype and phenotype. Nat Genet. 2009. 41(9):958-9.
43. Gregersen P K, Klein G, Keogh M, Kern M, DeFranco M, Simpfendorfer K R, et al. The Genotype and Phenotype (GaP) registry: a living biobank for the analysis of quantitative traits. Immunol Res. 2015. 63(1-3):107-12.
44. Arruda M S, Petta C A, Abrão M S, Benetti-Pinto C L. Time elapsed from onset of symptoms to diagnosis of endometriosis in a cohort study of Brazilian women. Hum Reprod. 2003. 18(4):756-9.
45. Evans-Hoeker E, Lessey B A, Jeong J W, Savaris R F, Palomino W A, Yuan L, et al. Endometrial BCL6 over-expression in eutopic endometrium of women with endometriosis. Reprod Sci. 2016. 23(9):1234-41.
46. Hirsch M, Duffy J M N, Deguara C S, Davis C J, Khan K S. Diagnostic accuracy of Cancer Antigen 125 (CA125) for endometriosis in symptomatic women: A multi-center study. Eur J Obstet Gynecol Reprod Biol. 2017. 210:102-7.
47. Acimovic M, Vidakovic S, Milic N, Jeremic K, Markovic M, Milosevic-Djeric A, et al. Survivin and VEGF as novel biomarkers in diagnosis of endometriosis. J Med Biochem. 2016. 35(1):63-8.
48. Vodolazkaia A, Yesilyurt B T, Kyama C M, Bokor A, Schols D, Huskens D, et al. Vascular endothelial growth factor pathway in endometriosis: genetic variants and plasma biomarkers. Fertil Steril. 2016. 105(4):988-96. 49. Gagne D, Page M, Robitaille G, Hugo P, Gosselin D. Levels of vascular endothelial growth factor (VEGF) in serum of patients with endometriosis. Hum Reprod. 2003. 18(8):1674-80.
50. Matalliotakis I M, Vassiliadis S, Goumenou A G, Athanassakis I, Koumantakis G E, Neonaki M A, et al. Soluble ICAM-1 levels in the serum of endometriotic patients appear to be independent of medical treatment. J Reprod Immunol. 2001. 51(1):9-19.
51. Kuessel L, Wenzl R, Proestling K, Balendran S, Pateisky P, Yotova s, et al. Soluble VCAM-1/soluble ICAM-1 ratio is a promising biomarker for diagnosing endometriosis. Hum Reprod. 2017. 32(4):770-9.
52. Mosbah A, Nabiel Y, Khashaba E. Interleukin-6, intracellular adhesion molecule-1, and glycodelin A levels in serum and peritoneal fluid as biomarkers for endometriosis. Int J Gynaecol Obstet. 2016. 134(3):247-51.
53. Bohler H C, Gercel-Taylor C, Lessey B A, Taylor D D. Endometriosis markers: immunologic alterations as diagnostic indicators for endometriosis. Reprod Sci. 2007. 14(6):595-604.
54. Drosdzol-Cop A, Skrzypulec-Plinta V, Stojko R. Serum and peritoneal fluid immunological markers in adolescent girls with chronic pelvic pain. Obstet Gynecol Surv. 2012. 67(6):374-81.
55. Wu M-H, Hsiao K-Y, Tsai S-J. Endometriosis and possible inflammation markers. GMIT. 2015. 4(3):61-7.
56. Johnson N P, Hummelshoj L, Adamson G D, Keckstein J, Taylor H S, Abrao M S, et al. World Endometriosis Society consensus on the classification of endometriosis. Hum Reprod. 2017. 32(2):315-24.

What is claimed is:

1. A method of treating endometriosis in a subject comprising:
   a) obtaining an identification of the subject as in need of treatment of endometriosis, wherein the subject has been identified as having endometriosis by:
   (i) maintaining a stromal fibroblast cell (SFC), obtained from a menstrual discharge sample from the subject, under conditions permitting decidualization, quantifying a rate or extent of decidualization of the stromal fibroblast cell, and comparing the rate of decidualization to a control value of decidualization indicative of a subject without endometriosis, wherein a rate or extent of decidualization of the stromal fibroblast cell which is less than that of the control value of decidualization indicates that the subject has endometriosis; or (ii) quantitating expression of ALDH1A1 protein in a stromal fibroblast cell obtained from a menstrual discharge sample from the subject and comparing the expression quantitated to a control value of expression of the ALDH1A1 protein indicative of a subject without endometriosis, wherein an amount of expression quantitated less than the control value indicates that the subject has endometriosis;

and b) treating the subject so-identified as having endometriosis by performing a laproscopic surgery or hysterectomy, or administering an amount of a progestin, a gonadotropin-releasing hormone agonist or a birth control pill effective to treat endometriosis.

2. The method of claim 1, wherein the subject has been identified as having endometriosis by maintaining a stromal fibroblast cell, obtained from a menstrual discharge sample from the subject, under conditions permitting decidualization, quantifying a rate or extent of decidualization of the stromal fibroblast cell, and comparing the rate of decidualization to a control value of decidualization indicative of a subject without endometriosis, wherein a rate or extent of decidualization of the stromal fibroblast cell which is less than that of the control value of decidualization indicates that the subject has endometriosis.

3. The method of claim 2, wherein the menstrual discharge sample comprises menstrual blood.

4. The method of claim 2, further comprising obtaining the menstrual discharge sample from the subject.

5. The method of claim 2, wherein the stromal fibroblast cell is contacted with 8-Br-CAMP and one or more hormones to effect decidualization.

6. The method of claim 5, wherein the one or more hormones comprise 17-beta estradiol and medroxyprogesterone.

7. The method of claim 2, wherein the rate or extent of decidualization is quantified by measuring IGFBP-1 production by the stromal fibroblast cell.

8. The method of claim 2, wherein the SFC is identified so as being: CD45−/CD326−/CD31−/CD90+/CD105+/CD73+.

9. The method of claim 8, wherein the SFC is also CD140b+.

10. The method of claim 1, wherein the subject has been identified as having endometriosis by quantitating expression of ALDH1A1 proteins in a stromal fibroblast cell obtained from a menstrual discharge sample from the subject and comparing the expression quantitated to a control value of expression of the ALDH1A1 indicative of a subject without endometriosis, wherein an amount of expression quantitated less than the control value indicates that the subject has endometriosis.

11. The method of claim 10, wherein quantitating the ALDH1A1 proteins comprises measuring protein-encoding RNA levels.

* * * * *